(12) United States Patent
Kim et al.

(10) Patent No.: US 9,116,161 B2
(45) Date of Patent: Aug. 25, 2015

(54) FREE FATTY ACID PARTICLE DISPERSION SOLUTION AND PREPARATION METHOD THEREOF

(71) Applicant: KOREA RESEARCH INSTITUTE OF STANDARDS AND SCIENCE, Daejeon (KR)

(72) Inventors: Se Hwa Kim, Daejeon (KR); Eun-Soo Lee, Incheon (KR)

(73) Assignee: KOREA RESEARCH INSTITUTE OF STANDARDS AND SCIENCE, Daejeon (KR)

( * ) Notice: Subject to any disclaimer, the term of this patent is extended or adjusted under 35 U.S.C. 154(b) by 0 days.

(21) Appl. No.: 14/074,430

(22) Filed: Nov. 7, 2013

(65) Prior Publication Data

US 2014/0342460 A1    Nov. 20, 2014

(30) Foreign Application Priority Data

May 20, 2013 (KR) .......................... 10-2013-0056767

(51) Int. Cl.
*G01N 33/92* (2006.01)
(52) U.S. Cl.
CPC ...................................... *G01N 33/92* (2013.01)

(58) Field of Classification Search
CPC ...................................................... G01N 33/92
See application file for complete search history.

(56) References Cited

U.S. PATENT DOCUMENTS

| 7,473,693 B2 * | 1/2009 | Lindfors ................... 514/255.06 |
| 2011/0182999 A1 * | 7/2011 | Serizawa et al. .............. 424/502 |

FOREIGN PATENT DOCUMENTS

| EP | 0962812 A1 * | 12/1999 |
| WO | 2011/149854 A2 | 12/2011 |

OTHER PUBLICATIONS

Laws et al., "Differences in Insulin Suprression of Free Fatty Acid levels by Gender and Glucose Tolerance Status," Arteriosclerosis, Thrombosis and Vascular Biology, 1997, 17: 64-71.

\* cited by examiner

*Primary Examiner* — Yong Chu
*Assistant Examiner* — Ana Z Muresan
(74) *Attorney, Agent, or Firm* — Sughrue Mion, PLLC

(57) ABSTRACT

Provided is a preparation method of a free fatty acid particle dispersion solution, the preparation method including: a) dissolving fatty acid in a solvent to prepare a fatty acid solution; and b) injecting the fatty acid solution in a non-solvent having miscibility with the solvent to prepare a free fatty acid particle dispersion solution.

14 Claims, 5 Drawing Sheets

FREE FATTY ACID PARTICLE DISPERSION SOLUTION AND PREPARATION METHOD THEREOF

CROSS-REFERENCE TO RELATED APPLICATIONS

THIS APPLICATION CLAIMS PRIORITY UNDER 35 U.S.C. §119 TO KOREAN PATENT APPLICATION NO. 10-2013-0056767, FILED ON May 20, 2013, IN THE KOREAN INTELLECTUAL PROPERTY OFFICE, THE DISCLOSURE OF WHICH IS INCORPORATED HEREIN BY REFERENCE IN ITS ENTIRETY.

TECHNICAL FIELD

The following disclosure relates to a free fatty acid particle dispersion solution and a preparation method thereof, and more particularly, to a pure free fatty acid particle dispersion solution capable of maintaining a significantly stable dispersion state, and a preparation method thereof.

BACKGROUND

Most of the fatty acids bind to albumin in the bloodstream to move, but a small amount of free fatty acids (FFA) may be present in blood or tissue. As reported by A. Laws et al., (Arteriosclerosis, Thrombosis, and Vascular Biology), this fatty acid particle (FFA particle) induces a specific biological reaction in a body, but mechanism thereof was not almost known. The reason is that it is difficult to artificially prepare a pure FFA particle in vitro, and a size of the particle may be unstable due to spontaneous agglomeration of the FFA particles. Therefore, in order to conduct various researches into diseases caused by the FFA in vitro, a technology of preparing a pure free fatty acid nanoparticle dispersion solution having stable dispersibility in a water-based dispersive medium has been required.

RELATED ART DOCUMENT

Non-Patent Document (Non-Patent Document 1) Arteriosclerosis, Thrombosis, and Vascular Biology. 1997; 17: 64-71

SUMMARY

An embodiment of the present invention is directed to providing a pure free fatty acid particle dispersion solution and a preparation method thereof, and more particularly, to provide a pure free fatty acid particle dispersion solution capable of having significantly stable dispersibility and commercially easily and simply being prepared, and a preparation method thereof.

In one general aspect, there is provided a preparation method of a free fatty acid particle dispersion solution, the preparation method including: a) dissolving fatty acid in a solvent to prepare a fatty acid solution; and b) injecting the fatty acid solution in a non-solvent having miscibility with the solvent to prepare a free fatty acid particle dispersion solution.

Step b) may include b1) injecting the fatty acid solution in the non-solvent using a syringe while stirring the non-solvent.

Step b) may further include b2) filtering a first dispersion solution obtained by injecting the fatty acid solution in the non-solvent and containing the free fatty acid particles dispersed therein to remove free fatty acid particles having a size larger than that of a filter used in filtering the first dispersion solution.

A volume ratio of the fatty acid solution to the non-solvent may be 1:50 to 500.

The maximum particle size of the free fatty acid particles in the dispersion solution in step b) may be 800 to 1500 nm or less.

The free fatty acid particles may be free fatty acid nanoparticles.

An average particle size of the free fatty acid particles in the dispersion solution in step b) may be 1 to 500 nm.

In step b), the fatty acid solution may be injected at a flow rate of 0.1 to 2 m/s in the non-solvent.

In step b), at the time of injecting the fatty acid solution, the non-solvent may be stirred at 400 to 1000 rpm.

The fatty acid solution may contain fatty acid at a concentration of 0.01 to 0.5M.

The solvent may be lower alcohol having 1 to 5 carbon atoms.

The non-solvent may be one or at least two selected from deionized water, a cell culture medium, and a cell culture medium containing fetal bovine serum (FBS).

The free fatty acid may be one or at least two selected from linoleic acid, oleic acid, and palmitoleic acid.

In another general aspect, there is provided a free fatty acid particle dispersion solution in which free fatty acid nanoparticles having an average particle size of 1 to 500 nm are dispersed in a dispersion medium containing a non-solvent.

The maximum particle size of the free fatty acid nanoparticles may be 800 to 1500 nm or less.

The non-solvent may be one or at least two selected from deionized water, a cell culture medium, and a cell culture medium containing fetal bovine serum (FBS).

The free fatty acid particle dispersion solution may contain free fatty nanoparticles at a concentration of 0.1 to 0.7 mg/mL.

DETAILED DESCRIPTION OF EMBODIMENTS

Figure 1:
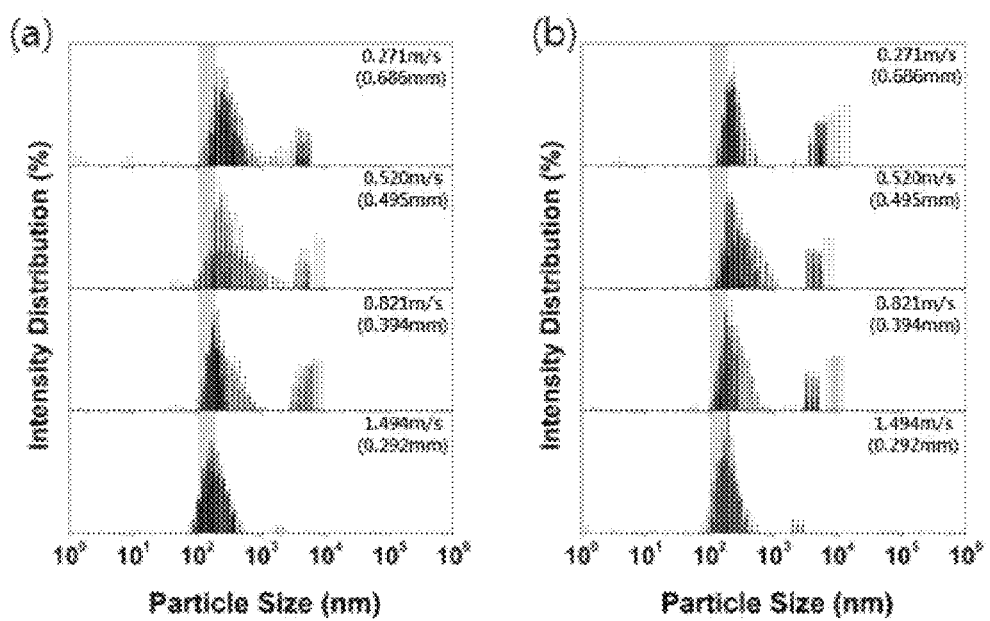
FIGS. 1A and 1B, which are views showing particle size distribution of free linoleic acid particle dispersion solution prepared according to an exemplary embodiment of the present invention, are views showing particle size distribution immediately after the particles are prepared and particle size distribution when the particles are left for 4 hours after being prepared, respectively.

Hereinafter, a dispersion solution according to the present invention and a preparation method thereof will be described in detail with reference to accompanying drawings. Here, technical terms and scientific terms used in the present specification have the general meaning understood by those skilled in the art to which the present invention pertains unless otherwise defined, and a description for the known function and configuration obscuring the present invention will be omitted in the following description and the accompanying drawings.

The present applicant tried to prepare pure free fatty acid (FFA) particle. As a result, the present applicant found that the FFA particle may be stably dispersed in a liquid medium in which a solvent dissolving fatty acid is mixed with a non-solvent not dissolving fatty acid but having miscibility with the solvent, and in the case of free fatty acid particles satisfying a specific condition, spontaneous agglomeration of the free fatty acid particles may be significantly prevented, such that size distribution may be significantly stably maintained, thereby applying the present invention.

A preparation method of a free fatty acid particle dispersion solution according to the present invention includes: a) dissolving fatty acid in a solvent to prepare fatty acid solution; and b) injecting the fatty acid solution in a non-solvent having miscibility with the solvent to prepare a free fatty acid particle dispersion solution.

In describing the present invention, the term "free fatty acid" may mean fatty acid in which reactivity due to a carboxylic acid group in the fatty acid is maintained, that is, the fatty acid in which the carboxyl group is not covalently bound with a heterogeneous functional group.

In detail, the fatty acid used as a raw material at the time of preparing the fatty acid solution in step a) may be pure fatty acid, more specifically, free fatty acid, and the free fatty acid particle dispersion solution obtained in step b) may be a dispersion solution of the pure fatty acid particles, more specifically, free fatty acid particles.

As a specific example, the fatty acid used as the raw material at the time of preparing the fatty acid solution in step a) may be one or at least two selected from linoleic acid, oleic acid, and palmitoleic acid, and the free fatty acid particles contained in the dispersion solution in step b) may be one or at least two selected from free linoleic acid particles, free oleic acid particles, and free palmitoleic acid particles.

As described above, in the preparation method of a free fatty acid particle dispersion solution according to the present invention, the free fatty acid particle may be prepared and at the same time, the dispersion solution in which a size of the free fatty acid particle is controlled may be prepared therefrom by a simple method of injecting the prepared fatty acid solution in the non-solvent after dissolving the fatty acid in the solvent to prepare the fatty acid solution. In this case, the non-solvent may be a material having miscibility with the solvent dissolving the fatty acid and not dissolving the fatty acid.

That is, the free fatty acid particle dispersion solution according to the present invention may contact with non-solvent during a process of injecting the fatty acid dissolved in the solvent in the non-solvent to thereby be particulated by phase change (phase change from a liquid phase dissolved in the solvent into a solid phase).

In addition, the contact between the fatty acid dissolved in the solvent and the non-solvent may be more easily and uniformly performed in a relatively short time by miscibility between the solvent and the non-solvent, such that the particle may be formed by simple injection, and significantly fine free fatty acid particle may be prepared. Further, an average particle size and particle size distribution may be easily adjusted by at least one easily controllable physical factor selected from a flow rate at which the fatty acid solution is injected in the non-solvent and a stirring rate of the non-solvent at the time of injecting the fatty acid solution.

As a specific example of the non-solvent having miscibility with the solvent, one or at least two may be selected from deionized water, a cell culture medium, and a cell culture medium containing fetal bovine serum (FBS). In this case, the cell culture medium may include a general medium used to artificially culture bacteria, cells, tissues, or the like, and a natural or artificial culture medium containing at least one nutrient selected from carbon sources, nitrogen sources, and growth factors including minerals and vitamins and selective containing antibiotics such as penicillin. In this case, the cell culture medium containing fetal bovine serum may contain 5 to 10 vol % of fetal bovine serum.

As in the specific example, since a water-based free fatty acid particle dispersion solution may be prepared by the preparation method according to the exemplary embodiment of the present invention, a biological reaction between the pure free fatty acid particles and another biochemical material and a mechanism thereof may be studied. In addition, as in the specific example, since a cell culture medium-based free fatty acid particle dispersion solution may be prepared by the preparation method according to the exemplary embodiment of the present invention, an environment similar to that in vivo may be composed, and a reaction occurring between free fatty acid and living cells or tissues and an influence of the free fatty acid may be clarified in vitro.

As the solvent, any material may be used as long as it may have miscibility with the above-mentioned non-solvent and dissolve pure fatty acid. As a specific example, the solvent may be lower alcohol having 1 to 5 carbon atoms. The lower alcohol may be monohydric, dihydric, or trihydric alcohol. The lower alcohol may be primary, secondary, or tertiary alcohol. The lower alcohol may be unsaturated or saturated alcohol.

In the case in which the non-solvent is water, or a cell culture medium, which is a material more suitable for studying reactivity between a free fatty acid particle and a biochemical material and an influence on organism, as the solvent, at least one of ethanol and methanol may be selected. At least one solvent selected from ethanol and methanol has significantly excellent miscibility with the non-solvent such as water or the cell culture medium and a significantly low boiling point as compared to the non-solvent, such that in the case of removing the solvent from the free fatty acid particle dispersion solution as needed, the solvent may be easily removed by volatilization at room temperature or a lower temperature (40° C.).

In the preparation method according to the exemplary embodiment of the present invention, the fatty acid solution may contain the solvent and pure fatty acid, more specifically, contain only the solvent and pure fatty acid but does not contain a heterogeneous material binding to the carboxylic group of the fatty acid to secure dispersibility of the fatty acid.

In the preparation method according to the exemplary embodiment of the present invention, the fatty acid solution may contain the fatty acid at a concentration of 0.01 to 0.5M. The mole concentration of the fatty acid contained in the fatty acid solution may affect the average size and distribution of free fatty acid particles to be prepared. In the case in which the mole concentration is less than 0.01M, fine free fatty acid particles having a size of several to several ten nanometers may be formed, but the particle distribution may become wide. In addition, a production rate of the free fatty acid particle may be excessively decreased. In the case in which the mole concentration of the fatty acid contained in the fatty acid solution is more than 0.5M, a content of the free fatty acid particle in the dispersion solution may be increased, which may increase the production rate, but large free fatty acid particles having a size of several hundred micrometers may be formed instead of the fine free fatty acid particles having a size of several to several ten nanometers. In view of preparing the fatty acid particles having a size of several nanometers to several micrometers and narrow particle size distribution and improving productivity, the mole concentration of the fatty acid in the fatty acid solution may be 0.01 to 0.5M, specifically 0.01 to 0.3M, and more specifically, 0.01 to 0.1M.

In the preparation method according to the exemplary embodiment of the present invention, at the time of injecting the fatty acid solution in the non-solvent having miscibility with the solvent of the fatty acid solution, a volume ratio of the fatty acid solution to the non-solvent may be 1:50 or more, more specifically 1:50 to 500. As the solvent and non-solvent of the fatty acid solution have miscibility with each other, the fatty acid of the fatty acid solution instantly contacts with the non-solvent by injection pressure when the fatty acid solution is injected in the non-solvent to thereby be particulated, but after a certain time, a dispersion medium of the free fatty acid particle dispersion solution becomes a mixed liquid medium in which the fatty acid solvent and the non-solvent are uniformly mixed with each other. Therefore, in the case in which the volume ratio of the non-solvent to the fatty acid solution is less than 50, it is impossible to exclude an influence by the solvent of the fatty acid solution in the dispersion medium of the dispersion solution. That is, significantly fine fatty acid particles may be dissolved again by the solvent contained in the dispersion medium. In addition, at the time of injecting the fatty acid solution, since driving force for particulating the fatty acid (phase transformation into the solid phase particles) is derived from the non-solvent, it is preferable that the driving force by the non-solvent is uniformly and homogeneously maintained until injection of the fatty acid solution is finished. In the case in which the volume ratio of the non-solvent to the fatty acid solution is less than 50, the driving force for phase transformation by the non-solvent may be changed while the fatty acid solution is injected. Therefore, the volume ratio of the non-solvent to the fatty acid solution is preferably 1:50 or more so as to exclude the influence of the solvent of the fatty acid solution in the dispersion medium and secure the driving force for uniform and homogeneous phase transformation at the time of injecting the fatty acid solution. When the fatty acid solution is injected into the non-solvent, it is preferable that the fatty acid solution is injected into the non-solvent so as to satisfy the above-mentioned volume ratio, but substantially, the upper limit of volume ratio of the non-solvent to the fatty acid solution may be 500.

The present applicant found that dispersion stability of the free fatty acid particle in the dispersion solution is significantly changed according to the size of the free fatty acid particle. That is, the present applicant found that when the free fatty acid particle is a nanoparticle, even in the case of the water-based dispersion medium, self-agglomeration of the free fatty acid may be significantly prevented, such that the free fatty acid particle may have excellent dispersion stability.

In detail, in the preparation method according to the exemplary embodiment of the present invention, the average particle size of the free fatty acid particles in the dispersion solution in step b) may be 1 to 500 nm. In the case in which the average particle size (average diameter) of the free fatty acid particles in the dispersion solution in step b) is 1 to 500 nm, specifically, 1 to 450 nm, more specifically, 1 to 250 nm, and furthermore specifically, 1 to 100 nm, the self-agglomeration of the free fatty acid may be significantly prevented. Therefore, when the dispersion solution is left at 37° C. for 24 hours, an average size change ((average particle size after being left for 24 hours−average particle size immediately after being prepared)/average particle size immediately after being prepared×100) of the free fatty acid particles may be maintained within 2.6%.

In detail, in the preparation method according to the exemplary embodiment of the present invention, the maximum particle size of the free fatty acid particles in the dispersion solution in step b) may be 800 to 1500 nm. This is based on the fact that in the case in which the free fatty acid particle is a fine particle (nanoparticle), self-agglomeration of free fatty acid is significantly prevented, thereby obtaining excellent dispersion stability. When the dispersion solution containing free fatty acid particles having size distribution in a range of several ten nanometers to several micrometers is left at 37° C. for 4 hours, particle size distribution of the free fatty acid particles may be divided into a first peak of 800 to 1500 nm or less and a second peak of 800 to 150 nm or more, based on 800 to 1500 nm. In the case of particles having an initial size more than 800 to 1500 nm, sizes thereof are gradually increased, but in the case of particles having of 800 to 1500 nm or less may stably maintain its distribution. The maximum particle size of the free fatty acid particle in the dispersion solution may be specifically 900 to 1300 nm or less, more specifically, 900 to 1100 nm or less, and furthermore specifically, 1000 nm or less.

That is, coarse free fatty acid particles of which sizes are changed by self agglomeration in the dispersion solution with the passage of the time may be particles having a size of 800 to 1500 nm or more, specifically, 900 to 1300 nm or more, more specifically, 900 to 1100 nm or more, and furthermore specifically, 1000 nm or more.

In the present invention, as the dispersion solution in which the free fatty acid particles are dispersed by injecting the fatty acid solution in the non-solvent having miscibility with the solvent, the average particle size and distribution of the fatty acid particles may be easily controlled by at least one easily controllable factor selected from the flow rate of the fatty acid solution and the stirring rate of the non-solvent.

More specifically, in the preparation method according to the exemplary embodiment of the present invention, the fatty acid solution may be injected in the non-solvent at a flow rate of 0.1 to 2 m/s in step b). As described above, the flow rate at which the fatty acid solution is injected in the non-solvent may affect the average particle size and distribution of the free fatty acid particles. Free fatty acid nanoparticles having an average particle size of 1 to 500 nm may be formed by injecting the fatty acid solution in the non-solvent at the flow rate of 0.1 to 2 m/s. In the case of injecting the fatty acid solution in the non-solvent at the above-mentioned flow rate, in view of size distribution of the free fatty acid particles, the free fatty acid particles having particle size distribution within an average particle size of at least 1 to 500 nm to thereby correspond to the first peak may be prepared. In this case, in view of size distribution of the free fatty acid particles, free fatty acid particles having an average particle size larger than 500 nm to thereby correspond to the second peak may be formed simultaneously with the particles corresponding to the first peak, but formation of the second peak may be prevented or an amount of the free fatty acid particles corresponding to the second peak may be minimized by injecting the fatty acid solution in the non-solvent at the flow rate of 0.1 to 2 m/s, specifically 0.2 to 2 m/s, and more specifically 0.8 to 2 m/s. In this case, at the time of injecting the fatty acid solution, a diameter of a solution outlet through which the fatty acid solution is injected at the above-mentioned flow rate may be 0.1 to 1 mm, specifically 0.25 to 0.8 mm, more specifically, 0.3 to 0.7 mm.

More specifically, in the preparation method according to the exemplary embodiment of the present invention, at the time of injecting the fatty acid solution in step b), the non-solvent may be stirred at 400 to 1000 rpm. Free fatty acid particles having narrow size distribution may be prepared by stirring the non-solvent at 400 to 1000 rpm at the time of injecting the fatty acid solution. In detail, formation of the above-mentioned coarse free fatty acid particles may be prevented or minimized by injecting the fatty acid solution at a flow rate of 0.1 to 2 m/s in the non-solvent stirred at 400 to 1000 rpm.

In the preparation method according to the exemplary embodiment of the present invention, injection of the fatty acid solution may be performed using a syringe. That is, step b) may include: b1) injecting the fatty acid solution in the non-solvent using a syringe while stirring the non-solvent. In this case, a diameter of a solution outlet of the syringe may be 0.1 to 1 mm, specifically 0.25 to 0.8 mm, more specifically 0.3 to 0.7 mm, and gauge pressure in the syringe (absolute pressure−atmospheric pressure) may be pressure at which the fatty acid solution is injected at a flow rate of 0.1 to 2 m/s.

As described above, when the free fatty acid particles are nanoparticles, spontaneous agglomeration between the free fatty acids may be significantly prevented, such that significantly stable dispersion state may be maintained. In the case of fine free fatty acid particles having a specific size, in detail, 800 to 1500 nm or less, the particle size may be hardly changed with the passage of time.

Therefore, in the preparation method of a free fatty acid particle dispersion solution according to the exemplary embodiment of the present invention, step b) may further include: b2) filtering a first dispersion solution obtained by injecting the fatty acid solution in the non-solvent and containing the free fatty acid particle dispersed therein to remove free fatty acid particles having a size larger than that of a filter used in filtering the first dispersion solution.

That is, when the free fatty acid particles are formed by injecting the fatty acid solution in the non-solvent, even though the free fatty acid particles has unimodal size distribution, a trace amount of coarse free fatty acid particles that may spontaneously agglomerate with the passage of time may be formed. In addition, when the free fatty acid particles are formed by injecting the fatty acid solution in the non-solvent, the free fatty acid particles having a relatively large average particle size as compared to the first peak to thereby correspond to the second peak may be formed together with the fine free fatty acid particles having an average particle size of 1 to 500 nm to thereby corresponding to the first peak in view of the particle size distribution. These coarse free fatty acid particles and/or free fatty acid particles corresponding to the second peak may deteriorate entire dispersion stability of the dispersion solution.

The entire dispersion stability of the free fatty acid particle dispersion solution may be secured by removing these coarse free fatty acid particles and/or free fatty acid particles corresponding to the second peak.

As described above, the free fatty acid particles deteriorating the dispersion stability may be performed by filtering the first dispersion solution corresponding to the dispersion solution obtained by injecting the fatty acid solution in the non-solvent and containing the free fatty acid particle dispersed therein to remove the free fatty acid particles having a size larger than that of the filter used in filtering the first dispersion solution.

The size of the filter used in filtering may be 1500 nm or less, specifically 1300 nm or less, more specifically, 1100 nm or less, more specifically, 1000 nm or less, and furthermore specifically, 800 nm or less. As a substantial example, the size of the filter may be 50 to 500 nm.

As described above, the dispersion stability of the free fatty acid dispersion solution may be further improved by filtering the first dispersion solution to separate and remove the free fatty acid particles having a size larger than a specific size to thereby deteriorate dispersion stability.

In detail, the preparation method according to the exemplary embodiment of the present invention may include: b1) injecting the fatty acid solution in the non-solvent using a syringe while stirring the non-solvent to prepare a first dispersion solution; and b2) filtering the first dispersion solution in step b1) to remove free fatty acid nanoparticles having a size larger than that of a filter used in filtering the first dispersion solution.

Further, the preparation method according to the exemplary embodiment of the present invention may further include: separating and recovering the free fatty acid particles from the free fatty acid particle dispersion solution obtained in step b) and then re-dispersing the recovered free fatty acid in the above-mentioned non-solvent.

Furthermore, the preparation method according to the exemplary embodiment of the present invention may further include: adding a non-solvent to the free fatty acid particle dispersion solution obtained in step b) to control a concentration of the free fatty acid particles in the dispersion solution. In this case, the non-solvent added to the free fatty acid particle dispersion solution may be the same as or different from the non-solvent in step b) and be a non-solvent having miscibility with the above-mentioned solvent. As a specific example, the non-solvent may be one or at least two selected from deionized water, a cell culture medium, and a cell culture medium containing fetal bovine serum (FBS).

The present invention includes free fatty acid nanoparticle dispersion solution.

The free fatty acid nanoparticle dispersion solution according to the present invention may be a dispersion solution in which free fatty acid nanoparticles having an average particle size of 10 to 500 nm are dispersed in a dispersion medium containing a non-solvent.

"Free fatty acid" of the free fatty acid nanoparticles may mean fatty acid in which reactivity due to a carboxylic acid group in the fatty acid is maintained, that is, the fatty acid in which the carboxylic group is not covalently bound with a heterogeneous functional group.

The average particle size and/or size distribution of the free fatty acid nanoparticles may be values measured using a dynamic light scattering (DLS) method. In detail, the average particle size and/or size distribution may be values measured at 37° C. using a 1 ml of sample (solution to be analyzed).

Generally, it was known that in the case of free fatty acids, particle sizes thereof are unstable due to the spontaneous agglomeration. However, in the dispersion solution according to the present invention, since the free fatty acid nanoparticles having an average particle size of 10 to 500 nm are dispersed in the non-solvent, the dispersion solution may have significantly excellent dispersion stability.

In detail, as the free fatty acid nanoparticles having an average particle size of 1 to 500 nm, specifically, 1 to 450 nm, more specifically, 1 to 250 nm, and furthermore specifically, 1 to 100 nm are dispersed in the dispersion solution according to the present invention, the self-agglomeration of the free fatty acid may be significantly prevented, such that, when the dispersion solution is left at 37° C. for 24 hours, an average size change ((average particle size after being left for 24 hours–average particle size immediately after being prepared)/average particle size immediately after being prepared×100) of the free fatty acid particles may be maintained within 2.6%.

In the dispersion solution according to the exemplary embodiment of the present invention, the free fatty acid nanoparticles may be one or at least two selected from free linoleic acid nanoparticles, free oleic acid nanoparticles, and free palmitoleic acid nanoparticles.

In the dispersion solution according to the exemplary embodiment of the present invention, the maximum particle size of the free fatty acid nanoparticles contained in the dispersion solution may be 800 to 1500 nm or less, specifically 900 to 1300 nm or less, more specifically, 900 to 1100 nm or less, and furthermore specifically, 1000 nm or less. Therefore, the dispersion solution does not contain free fatty acid nanoparticles having a coarse size causing agglomeration between free fatty acid nanoparticles, even in the case of storing the dispersion solution for a long period of time, particle size distribution of the free fatty acid nanoparticles may be maintained similarly or equally to that immediately after preparation.

In the dispersion solution according to the exemplary embodiment of the present invention, the dispersion medium may contain the non-solvent, and as the non-solvent, one or at least two may be selected from deionized water, a cell culture medium, and a cell culture medium containing fetal bovine serum (FBS). In this case, the cell culture medium may include a general medium used to artificially culture bacteria, cells, tissues, or the like, and a natural or artificial culture medium containing at least one nutrient selected from carbon sources, nitrogen sources, and growth factors including minerals and vitamins and selective containing antibiotics such as penicillin. In this case, the cell culture medium containing fetal bovine serum may contain 5 to 10 vol % of fetal bovine serum.

As in the specific example, since the dispersion solution according to the exemplary embodiment of the present invention may be a water-based free fatty acid particle dispersion solution, a biological reaction between the pure free fatty acid particles and another biochemical material and a mechanism thereof may be studied using the dispersion solution. In addition, as in the specific example, since the dispersion solution according to the exemplary embodiment of the present invention may be a cell culture medium-based free fatty acid particle dispersion solution, an environment similar to that in vivo may be composed, and a reaction occurring between free fatty acid and living cells or tissues and an influence of the free fatty acid thereon may be clarified in vitro.

In the dispersion solution according to the exemplary embodiment of the present invention, the dispersion medium may contain only a pure non-solvent, or contain a non-solvent and a solvent dissolving fatty acid and having miscibility with the non-solvent. Describing the present invention in detail in relation to the above-mentioned preparation method, a dispersion solution in which the free fatty acid particles are dispersed in the dispersion medium purely composed of only the non-solvent may be prepared by further performing the removing of the solvent by volatilizing the solvent using a difference in boiling points between the non-solvent and the solvent after performing step b). Describing the present invention in detail in relation to the above-mentioned preparation method, in the case in which the removing of the solvent by volatilizing is not performed after performing step b), a mixed solution of the non-solvent and the solvent may form the dispersion medium.

In the case in which the dispersion medium contains the non-solvent and the solvent having miscibility with the non-solvent, the solvent may be lower alcohol having 1 to 5 carbon atoms. The lower alcohol may be monohydric, dihydric, or trihydric alcohol. The lower alcohol may be primary, secondary, or tertiary alcohol. The lower alcohol may be unsaturated or saturated alcohol. In detail, as the lower alcohol, at least one may be selected from ethanol and methanol. In this case, a volume ratio of the solvent to the non-solvent in the dispersion medium may be 1:50 to 500.

In the dispersion solution according to the exemplary embodiment of the present invention, the free fatty acid nanoparticle dispersion solution may contain the free fatty acid nanoparticles at a concentration of 0.2 to 0.8 mg/mL.

Hereinafter, the present invention will be described based on Preparation Examples, but this Preparation Example is provided for experimentally demonstrating excellence of the present invention and assisting in the entire understanding of the present invention. Therefore, the present invention is not limited to the following Preparation Example.

A linoleic acid stock solution having a concentration of 1M was prepared by dissolving linoleic acid in 100% ethanol. A linoleic acid solution having a concentration of 0.04M, 0.06M, 0.1M, 0.175M, 0.25M, or 0.5M was prepared by diluting the prepared stock solution in ethanol. The prepared linoleic acid solution was stored at −20° C., and in the case of storing the solution for 7 days or more, the solution was discarded, and the linoleic acid solution was prepared again from the stock solution.

As a non-solvent, deionized water, a cell culture medium (Dulbecco's Modified Eagle Medium, Gibco Corp., Product No. 11965-092), or a cell culture medium containing 10 vol % of fetal bovine serum (FBS) was used.

After 0.1 mL of 0.1M linoleic acid solution was defrosted at 37° C. for 10 minutes and stirred in vortex, the stirred linoleic acid solution was injected in 10 mL of the non-solvent using a syringe having a diameter of an outlet (a diameter of a needle) of 0.686 mm, 0.495 mm, 0.394 mm, or 0.292 mm so as to have an injection flow rate of 0.271 m/s, 0.520 m/s, 0.821 m/s, or 1.494 m/s, thereby preparing a free linoleic acid nanoparticle dispersion solution. Here, at the time of injecting the linoleic acid solution using the syringe, the non-solvent was stirred at 500 rpm.

Thereafter, the dispersion solution was filtered using a filter having a diameter of 450 nm, 220 nm, or 100 nm, thereby removing particles having a size larger than 450 nm, 220 nm, or 100 nm from the prepared dispersion solution.

The average particle size and/or size distribution of the free fatty acid nanoparticles in the dispersion solution were values measured using a dynamic light scattering (DLS) method. In detail, the average particle size and/or size distribution were values measured at 37° C. using a 1 ml of sample (solution to be analyzed).

FIGS. 1A and 1B show results of particle size distribution of free linoleic acid nanoparticle dispersion solution (that was not filtered yet) prepared by injecting the linoleic acid solution having a concentration of 0.1M in a cell medium containing fetal bovine serum (FBS) at a flow rate of 0.271 m/s, 0.520 m/s, 0.821 m/s, or 1.494 m/s, wherein FIG. 1A shows results of particle size distribution measured immediately after the particles are prepared, and FIG. 1B shows results of particle size distribution measured after the particles are left at 37° C. for 4 hours after being prepared. In this case, a diameter of the needle of the syringe was recorded in parenthesis together with an injection flow rate of the linoleic acid solution of each sample in FIG. 1.

As shown in FIGS. 1A and 1B, it may be appreciated that linoleic acid particles having a relatively small size in a first peak and having a relatively large size in a second peak were prepared, and in the case of linoleic acid nanoparticles corresponding to the first peak (average particle size of about 170 nm), having a relative small size within an average particle size of 250 to 500 nm, even though they were left at 37° C. for 4 hours, there was almost no change in particle size and distribution. In addition, it may be appreciated that in the case of linoleic acid nanoparticles corresponding to the second peak, having a relative large size, agglomeration between the particles was generated, and with the passage of time, the distribution was divided into distribution of linoleic acid nanoparticles having stable dispersibility and distribution of macro-particles in which agglomeration was generated based on the size of about 1000 nm.

Figure 2:
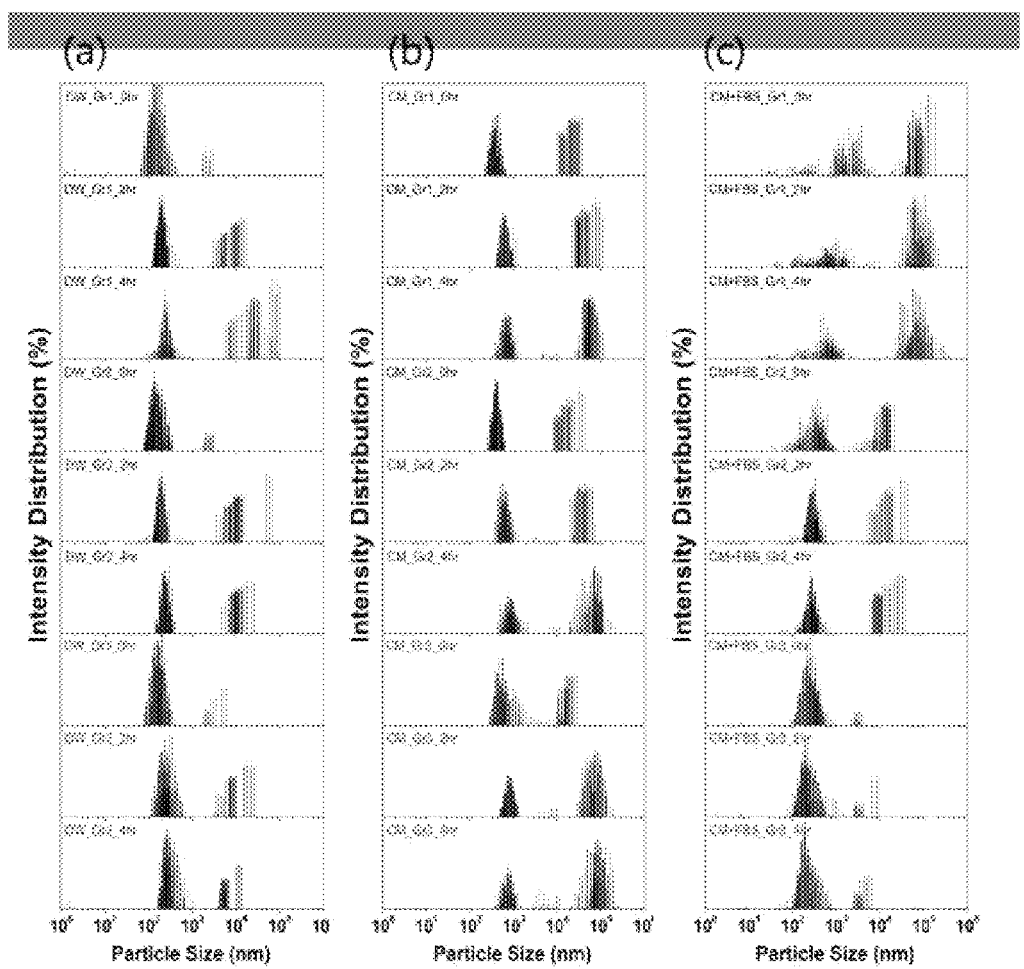
FIGS. 2A to 2C are views showing results obtained by measuring particle size distribution of free linoleic acid particle dispersion solution in free linoleic acid particle dispersion solutions prepared according to the exemplary embodiment of the present invention according to a kind of non-solvents.

FIGS. 2A to 2C are view showing results obtained by measuring dispersion stability of a free linoleic acid nanoparticle dispersion solution prepared using deionized water (represented by DW in FIGS. 2A to 2C), a cell culture medium (represented by CM in FIGS. 2A to 2C), or a cell culture medium containing 10 vol % of serum (represented by CM+FBS in FIGS. 2A to 2C) as the non-solvent according to the time. In FIGS. 2A to 2C, DW means a sample using deionized water, CM means a sample using the cell culture medium, and CM+FBS means a sample using the cell culture medium containing fetal bovine serum as the non-solvent, respectively. In addition, Gr1 means a sample using a linoleic acid solution having a concentration of 0.25M, Gr2 means a sample using a linoleic acid solution having a concentration of 0.175M, and Gr3 means a sample using a linoleic acid solution having a concentration of 0.1M, and 0 hr, 2 hr, and 4 hr mean that measurement was performed immediately after preparation, after 2 hours of preparation, and after 4 hours of preparation. All of the samples used in measurement of FIGS. 2A to 2C were prepared using a syringe having a needle diameter of 0.394 mm and at an injection flow rate of 0.821 m/s.

In all kinds of dispersion solutions, it may be confirmed that in the case in which macro-particles coexisted, self agglomeration of the macro-particles were generated.

Figure 3:
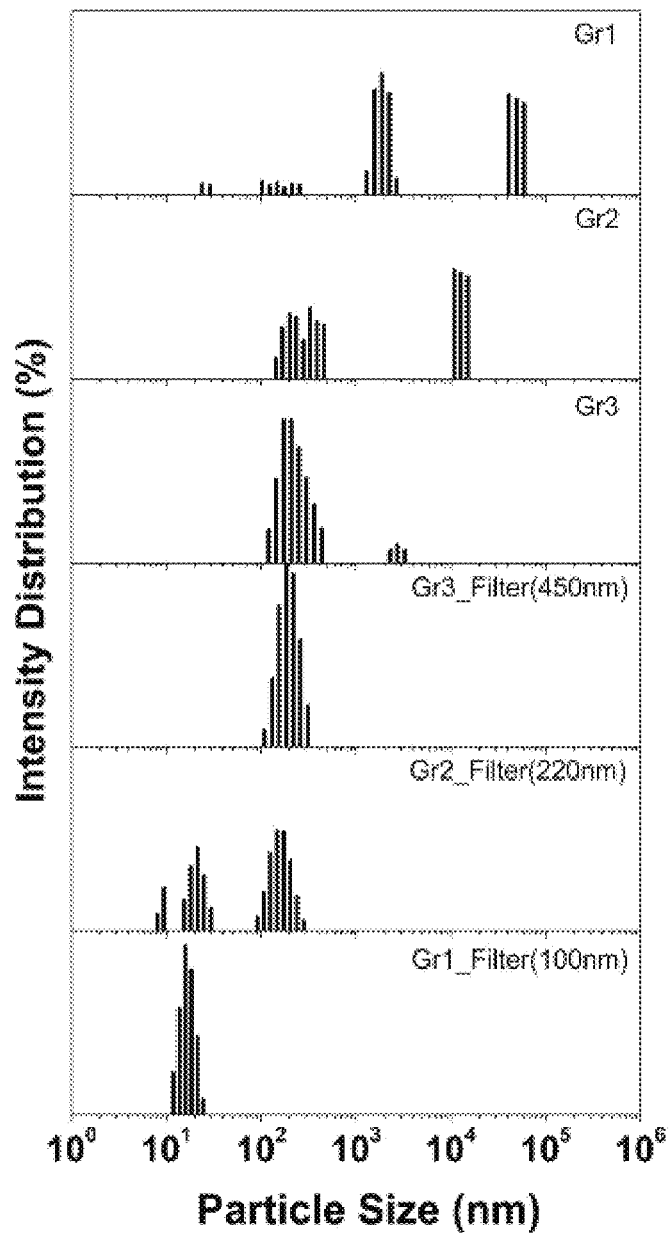
FIG. 3 is a view showing particle size distribution of a dispersion solution filtered using a filter after preparing a free linoleic acid particle dispersion solution according to another exemplary embodiment of the present invention.

FIG. 3 shows results of particle size distribution of a dispersion solution (Gr1_Filter(100 nm) of FIG. 3) prepared by filtering a Gr1 sample of a free linoleic acid nanoparticle dispersion solution (Gr1 of FIG. 3) prepared by injecting a linoleic acid solution having a concentration of 0.25M in deionized water using a filter (100 nm), a dispersion solution (Gr2_Filter(220 nm) of FIG. 3) prepared by filtering a Gr2 sample of a free linoleic acid nanoparticle dispersion solution (Gr2 of FIG. 3) prepared by injecting a linoleic acid solution having a concentration of 0.175M in deionized water using a filter (220 nm), and a dispersion solution (Gr3_Filter(450 nm) of FIG. 3) prepared by filtering a Gr3 sample of a free linoleic acid nanoparticle dispersion solution (Gr3 in FIG. 3) prepared by injecting a linoleic acid solution having a concentration of 0.1M in deionized water using a filter (450 nm). In this case, the Gr1, Gr2, and Gr3 samples used in measurement of FIG. 3 were prepared using a syringe having a needle diameter of 0.394 mm and at an injection flow rate of 0.821 m/s.

As shown in FIG. 3, the free linoleic acid nanoparticles having a size deteriorating dispersion stability due to self agglomeration may be removed by filtering, and the free linoleic acid nanoparticle dispersion solution having more excellent stability may be prepared.

Figure 4:
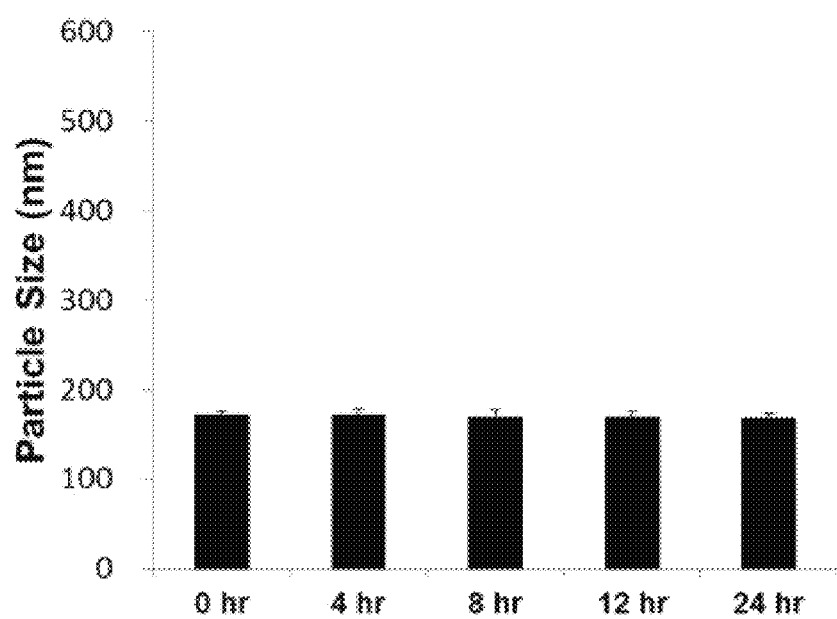
FIG. 4 is a view showing particle size distribution in a dispersion solution when the free linoleic acid particle dispersion solution prepared according to the exemplary embodiment of the present invention is left for 24 hours.

FIG. 4 shows results obtained by measuring an average particle size of the dispersion solution immediately after the Gr3_Filter(450 nm) sample of FIG. 3 was prepared, and after the sample was left at 37° C. for 4 hours, 8 hours, 12 hours, or 24 hours. The average particle size (average) and standard deviation (STDEV) according to the leaving time were shown in the following Table 1. As shown in Table 1, it may be appreciated that the particle size was uniformly maintained.

TABLE 1

| | Time | | | | |
| --- | --- | --- | --- | --- | --- |
| | 0 hr | 4 hr | 8 hr | 12 hr | 24 hr |
| Average (nm) | 173.0 | 172.3 | 170.5 | 169.8 | 168.5 |
| STDEV | 3.3 | 5.9 | 6.1 | 6.0 | 5.1 |

Figure 5:
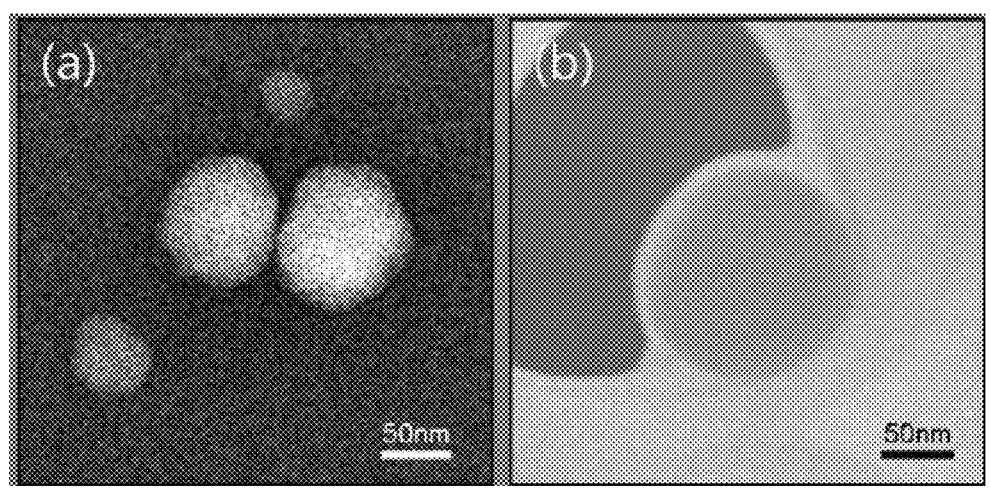
FIGS. 5A and 5B are transmission electronic microscope (TEM) photographs of the free linoleic acid particles prepared according to the exemplary embodiment of the present invention.

FIGS. 5A and 5B are transmission electron microscope photographs of the prepared free linoleic acid nanoparticles, and it may be appreciated that pure free linoleic acid was formed as spherical nanoparticles.

With a preparation method according to the present invention, free fatty acid particles and a free fatty acid particle dispersion solution having significantly excellent dispersion stability may be simultaneously prepared by a simple method of dissolving fatty acid in a solvent to prepare a fatty acid solution and then injecting the prepared fatty acid solution in a non-solvent having miscibility with the solvent.

Hereinabove, although the present invention is described by specific matters, exemplary embodiments, and drawings, they are provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to the above-described exemplary embodiments, and the following claims as well as all modified equally or equivalently to the claims are intended to fall within the scope and spirit of the invention.

What is claimed is:

1. A method for preparing a dispersion solution of free fatty acid particles, said preparation method comprising:
 a) dissolving free fatty acid in a solvent to prepare a fatty acid solution, said fatty acid solution consisting of the free fatty acid and the solvent; and
 b) injecting the fatty acid solution into a non-solvent medium having miscibility with the solvent to prepare the dispersion solution of free fatty acid particles;
 wherein free fatty acid particles consisting of the free fatty acid are dispersed in a dispersion medium comprising the non-solvent medium.

2. The method of claim 1, wherein step b) includes injecting the fatty acid solution in the non-solvent medium using a syringe while stirring the non-solvent medium.

3. The method of claim 1, which further includes filtering the dispersion solution of free fatty acid particles remove free fatty acid particles having a size larger than pore size of a filter used in filtering the dispersion solution.

4. The method of claim 1, wherein a volume ratio of the fatty acid solution:the non-solvent is 1:50-1:500.

5. The method of claim 1, wherein the particle size of the free fatty acid particles in the dispersion solution in step b) is 800 to 1500 nm.

6. The method of claim 1, wherein the free fatty acid particles are free fatty acid nanoparticles.

7. The method of claim 6, wherein an average particle size of the free fatty acid particles in the dispersion solution in step b) is 1 to 500 nm.

8. The method of claim 1, wherein in step b), the fatty acid solution is injected at a flow rate of 0.1 to 2 m/s.

9. The method of claim 8, wherein in step b), at the time of injecting the fatty acid solution, the non-solvent is stirred at 400 to 1000 rpm.

10. The method of claim 9, wherein the fatty acid solution contains the fatty acid at a concentration of 0.01 to 0.5M.

11. The method of claim 1, wherein the solvent is a lower alcohol having 1 to 5 carbon atoms.

12. The method of claim 1, wherein the non-solvent medium is one or more selected from the group consisting of deionized water, a cell culture medium, and a cell culture medium containing fetal bovine serum.

13. The method of claim 1, wherein the free fatty acid is one or more selected from the group consisting of linoleic acid, oleic acid, and palmitoleic acid.

14. The method of claim 1, which further comprises removing the solvent from the dispersion solution of free fatty acid particles obtained in step b).

\* \* \* \* \*